United States Patent
Gane et al.

(10) Patent No.: US 8,871,057 B2
(45) Date of Patent: *Oct. 28, 2014

(54) PROCESS FOR THE PRODUCTION OF NANO-FIBRILLAR CELLULOSE SUSPENSIONS

(75) Inventors: Patrick A. C. Gane, Rothrist (CH); Joachim Schoelkopf, Killwangen (CH); Daniel Gantenbein, Basel (CH); Michel Schenker, Oftringen (CH); Michael Pohl, Villach (AT); Beat Kübler, Oberwil (CH)

(73) Assignee: Omya International AG, Oftringen (CH)

( * ) Notice: Subject to any disclaimer, the term of this patent is extended or adjusted under 35 U.S.C. 154(b) by 53 days.

This patent is subject to a terminal disclaimer.

(21) Appl. No.: 13/138,647

(22) PCT Filed: Mar. 30, 2010

(86) PCT No.: PCT/EP2010/054231
§ 371 (c)(1),
(2), (4) Date: Oct. 14, 2011

(87) PCT Pub. No.: WO2010/112519
PCT Pub. Date: Oct. 7, 2010

(65) Prior Publication Data
US 2012/0094953 A1    Apr. 19, 2012

Related U.S. Application Data

(60) Provisional application No. 61/212,108, filed on Apr. 6, 2009.

(30) Foreign Application Priority Data

Mar. 30, 2009 (EP) .................................. 09156683

(51) Int. Cl.
| | | |
|---|---|---|
| D21H 21/00 | (2006.01) | |
| D21C 9/00 | (2006.01) | |
| D21B 1/16 | (2006.01) | |
| D21D 1/00 | (2006.01) | |
| D21H 11/18 | (2006.01) | |
| D21H 15/04 | (2006.01) | |

(52) U.S. Cl.
CPC D21B 1/16 (2013.01); D21C 9/007 (2013.01); D21D 1/00 (2013.01); D21H 15/04 (2013.01); D21H 11/18 (2013.01)
USPC .................... 162/181.1; 524/35; 162/181.2

(58) Field of Classification Search
USPC ............................ 524/35; 162/181.1, 181.2
See application file for complete search history.

(56) References Cited

U.S. PATENT DOCUMENTS 2,169,473 A * 8/1939 Olsen .............................. 162/11
2,583,548 A * 1/1952 Craig .......................... 162/181.2
(Continued)

FOREIGN PATENT DOCUMENTS

| | | | |
|---|---|---|---|
| CA | 2 437 616 A1 | 2/2005 | |
| EP | 0 726 356 A1 | 8/1996 | |

(Continued)

OTHER PUBLICATIONS

Campinhos, Jr. E., "Sustainable plantations of high-yield Eucalyptus trees for production of fiber: the Aracruz case." New Forests, 1999, 17, 129-143.*

(Continued)

Primary Examiner — Liam J Heincer
Assistant Examiner — Nicholas Hill
(74) Attorney, Agent, or Firm — Amster, Rothstein & Ebenstein LLP (57) ABSTRACT

The present invention relates to a process for the production of suspensions of nano-fibrillar cellulose by providing cellulose fibers and at least one filler and/or pigment; combining the cellulose fibers and the at least one filler and/or pigment; and fibrillating the cellulose fibers in the presence of at least one filler and/or pigment, as well as the suspensions of nano-fibrillar cellulose obtained by this process and their uses.

50 Claims, 4 Drawing Sheets

(56) References Cited

U.S. PATENT DOCUMENTS

| | | | |
|---|---|---|---|
| 3,730,830 A | | 5/1973 | Driscoll |
| 3,794,558 A | | 2/1974 | Back |
| 4,087,317 A | | 5/1978 | Roberts |
| 4,374,702 A | | 2/1983 | Turbak et al. |
| 4,426,258 A | * | 1/1984 | Browning .................. 162/23 |
| 4,474,949 A | | 10/1984 | Chatterjee et al. |
| 4,481,076 A | | 11/1984 | Herrick |
| 4,481,077 A | | 11/1984 | Herrick |
| 4,495,245 A | | 1/1985 | Zunker |
| 4,952,278 A | | 8/1990 | Gregory et al. |
| 5,156,719 A | * | 10/1992 | Passaretti .................. 162/158 |
| 5,531,821 A | | 7/1996 | Wu |
| 5,964,983 A | | 10/1999 | Dinand et al. |
| 6,074,524 A | | 6/2000 | Wu et al. |
| 6,159,335 A | | 12/2000 | Owens et al. |
| 6,183,596 B1 | | 2/2001 | Matsuda et al. |
| 6,214,163 B1 | | 4/2001 | Matsuda et al. |
| 6,436,232 B1 | | 8/2002 | Silenius et al. |
| 6,468,393 B1 | | 10/2002 | Small et al. |
| 7,381,294 B2 | | 6/2008 | Suzuki et al. |
| 7,462,232 B2 | | 12/2008 | Tuason et al. |
| 8,012,573 B2 | | 9/2011 | Kowata et al. |
| 8,231,764 B2 | | 7/2012 | Husband et al. |
| 2001/0045264 A1 | | 11/2001 | Rheims et al. |
| 2004/0108081 A1 | | 6/2004 | Hughes |
| 2004/0131854 A1 | | 7/2004 | Aho et al. |
| 2004/0168783 A1 | | 9/2004 | Munchow |
| 2005/0116010 A1 | | 6/2005 | Gronroos et al. |
| 2008/0023161 A1 | | 1/2008 | Gather |
| 2008/0060774 A1 | | 3/2008 | Zuraw et al. |
| 2008/0146701 A1 | | 6/2008 | Sain et al. |
| 2010/0272938 A1 | | 10/2010 | Mitchell et al. |
| 2010/0272980 A1 | | 10/2010 | Kowata et al. |
| 2011/0186252 A1 | | 8/2011 | Subramanian et al. |
| 2011/0259537 A1 | | 10/2011 | Husband et al. |
| 2011/0274908 A1 | | 11/2011 | Kowata et al. |
| 2011/0277947 A1 | | 11/2011 | Hua et al. |
| 2012/0043039 A1 | | 2/2012 | Paltakari et al. |
| 2012/0094953 A1 | | 4/2012 | Gane et al. |
| 2012/0107480 A1 | | 5/2012 | Gane et al. |
| 2012/0125547 A1 | | 5/2012 | Akai |
| 2012/0132383 A1 | | 5/2012 | Laine et al. |
| 2012/0216718 A1 | | 8/2012 | Berglund et al. |
| 2012/0277351 A1 | | 11/2012 | Yano et al. |
| 2012/0318471 A1 | | 12/2012 | Turkki et al. |
| 2013/0053454 A1 | | 2/2013 | Heiskanen et al. |
| 2013/0126112 A1 | | 5/2013 | Gane et al. |
| 2013/0133848 A1 | | 5/2013 | Heijnesson-Hulten et al. |
| 2013/0180680 A1 | | 7/2013 | Axrup et al. |
| 2013/0284387 A1 | | 10/2013 | Umemoto et al. |
| 2013/0345416 A1 | | 12/2013 | Laukkanen et al. |
| 2014/0058077 A1 | | 2/2014 | Laukkanen et al. |

FOREIGN PATENT DOCUMENTS

| | | |
|---|---|---|
| EP | 0 852 588 B1 | 7/1998 |
| EP | 0949294 A1 | 10/1999 |
| EP | 1 538 257 A1 | 6/2005 |
| EP | 2236545 A1 | 10/2010 |
| EP | 2236545 B1 | 10/2010 |
| EP | 2236664 A1 | 10/2010 |
| GB | 663 621 | 12/1951 |
| JP | 10237220 A | 9/1998 |
| JP | 2007262594 A | 10/2007 |
| TW | 200609278 | 3/2006 |
| WO | WO 98/56860 * | 12/1998 |
| WO | WO 02/090651 A1 | 11/2002 |
| WO | WO 03033815 A2 | 4/2003 |
| WO | 2010015726 A1 | 2/2010 |
| WO | 2010092239 A1 | 8/2010 |
| WO | 2010112519 | 10/2010 |
| WO | 2010115785 | 10/2010 |
| WO | WO 2010/115785 | 10/2010 |
| WO | 2010131016 A2 | 11/2010 |
| WO | 2011134938 A1 | 11/2011 |
| WO | 2011134939 A1 | 11/2011 |

OTHER PUBLICATIONS

Auad, M. L., et al., "Characterization of nanocellulose-reinforced shape memory polyurethanes," Polymer International, 2008, 57, 651-659. Online Publication Date: Dec. 13, 2007.*
Kenny, M., et al., "Lime and Limestone," Ullmann's Encyclopedia of Industrial Chemistry. 2012. vol. 21, 37-69.*
Dupont, A.-L., "Cellulose in lithium chloride/N,N-dimethylacetamide, optimisation of a disslution method using paper substrates and stability of the solutions," Polymer, 2003, 44, 4117-4126.*
Patt, R., et al., "Paper and Pulp," Ullmann's Encyclopedia of Industrial Chemistry. Published online: Jun. 2000.*
Falini, G., et al., "Oriented Crystallization of Vaterite in Collagenous Matrices," Chem. Eur. J., 1998, 4, 1048-1052.*
Third Party Observations dated May 27, 2011 for European Application No. 09156683.6.
The European Search Report dated Jun. 26, 2009 for European Application No. EP 09156683.6.
Sixta, "Handbook of Pulp." Wood Structure and Morphology, vol. 1, pp. 41 and 42.
Hubbe, "Mini-encyclopedia ofpPapermaking wet-end chemistry: Fibrillation." NC State University Internet Citation p. 1.
Hubbe et al. "What happens to cellulosic fibers during papermaking and recycling? A Review." BioResources 2(4): pp. 739-788.
Siró et al. "Microfibrillated cellulose and new nanocomposite materials: A Review." Cellulose (2010): 17, pp. 459-494.
International Search Report dated Jun. 7, 2010 for PCT Application No. PCT/EP2010/054231.
Written Opinion of the International Searching Authority for PCT Application No. PCT/EP2010/054231.
Office Action dated Sep. 24, 2012 for European Application No. 10711 423.3-2115.
Office Action dated Jan. 16, 2013 for Chinese Application No. 201080015262.5.
Little et al. "Hydrated Lime—more than just a filler." National Lime Association.
Third Party Observations dated Oct. 21, 2011 for European Application No. EP 09156703.2.
European Search Report dated Jun. 26, 2009 for European Application No. EP 09156703.2.
Office Action dated Jan. 28, 2014 for Japanese Application No. 2012-502646.
Examination Report dated Feb. 11, 2014 for Taiwanese Application No. 099109562.
First Office Action dated Oct. 23, 2013 for Chinese Application No. 201080015263.X.
Office Action for Russian Application No. 2011143811.
Office Action for Russian Application No. 2011143854.
Office Action dated Jan. 7, 2014 for Canadian Application No. 2,755,495.
Office Action for Ukrainian Application No. a 2011 12682.
Third Party Observations dated Jun. 6, 2012 for European Application No. EP 09156683.6.
Third Party Observations dated Oct. 21, 2011 for European Application No. EP 09156683.6.
European Search Opinion dated Jun. 26, 2009 for European Application No. EP 09156683.6.
Third Party Observations dated Jun. 6, 2012 for European Application No. EP 09156703.2.
Third Party Observations dated May 18, 2011 for European Application No. EP 09156703.2.
Third Party Observations dated Jun. 11, 2012 for European Application No. 10161166.3.
Communication dated Aug. 6, 2013 for European Application No. EP 11716257.8.
Response to the Communication dated Nov. 5, 2013 for European Application No. EP 11716257.8.

(56) References Cited

OTHER PUBLICATIONS

International Search Report dated Nov. 3, 2011 for PCT Application No. PCT/EP2011/056540.
Writen Opinion of the Internatonal Searching Authorty dated Oct. 27, 2012 for PCT Applicaton No. PCT/EP2011/056540.
Third Party Observations dated Jan. 9, 2012 for European Application No. EP 10161173.9.
Third Party Observations dated Jun. 11, 2012 for European Application No. EP 10161173.9.
Third Party Observations dated Apr. 19, 2013 for European Application No. EP 10161173.9.
Chauhan et al. "Use of Nanotechnology or High Performane Cellulosic and Papermaking Products." 2012, Cellulose Chemistry and Technology, 46(5-6), pp. 389-400.
Charani et al. "Rheological Characterization of High Concentrated MFC Gel from Kenaf Unbleached Pulp." 2013, Cellulose, vol. 20, pp. 727-740.
Opietnik et al. "TENCEL® Gel—A Novel Cellulose Micro Suspension." 2013, Lenzinger Berichte, vol. 91, pp. 89-92.
Shen et al. "Carbohydrate-based fillers and pigments for papermaking: A review" 2011, Carbohydrate Polymers, vol. 85, 17-22.
International Search Report dated Aug. 17, 2010 for PCT Application No. PCT/EP2010/054233.
Written Opinion of the International Searching Authority dated Sep. 30, 2011 for PCT Applicaton No. PCT/EP2010/054233.
Third Party Observations dated Jun. 11, 2012 for European Application No. EP 1073884.4.
Third Party Observations dated Feb. 17, 2012 for European Application No. EP 1073884.4.
Third Party Observations dated Jun. 11, 2012 for European Application No. EP 10711423.3.
Third Party Observations dated Feb. 17, 2012 for European Application No. EP 10711423.3.
Third Party Observations dated Feb. 4, 2013 for European Application No. EP 11716257.8.
Third Party Observations dated Feb. 4, 2013 for European Application No. EP 11719499.3.
Communication dated Jan. 2, 2014 for European Application No. EP 10713884.4.
Communication dated Feb. 21, 2013 for European Application No. EP 10713884.4.
Communication dated Jan. 2, 2014 for European Application No. EP 09156683.6.
Communication dated Jul. 31, 2013 for European Application No. EP 09156683.6.
Communication dated Feb. 7, 2013 for European Application No. EP 09156683.6.
Communication dated Jun. 27, 2011 for European Application No. EP 09156683.6.
Communication dated Jul. 31, 2013 for European Application No. EP 09156703.2.
Communication dated Feb. 7, 2013 for European Application No. EP 09156703.2.
Communication dated May 20, 2011 for European Application No. EP 09156703.2.
Communication dated Mar. 26, 2014 for European Application No. EP 10711423.3.
Communication dated Sep. 24, 2012 for European Application No. EP 10711423.3.
Communication dated Mar. 15, 2013 for European Application No. 10161166.3.
European Search Report dated Sep. 8, 2010 for European Application No. 10161166.3.
Communication dated Feb. 15, 2013 for European Application No. 11716257.
Communication dated Mar. 15, 2013 for European Application No. EP 10161173.9.
European Search Report dated Sep. 7, 2010 for European Application No. EP 10161173.9.
Communication dated Oct. 11, 2013 for European Application No. EP 1179499.

\* cited by examiner

PROCESS FOR THE PRODUCTION OF NANO-FIBRILLAR CELLULOSE SUSPENSIONS

This is a U.S. national phase of PCT Application No. PCT/EP2010/054231, filed Mar. 30, 2010, which claims priority to European Patent Application No. 09156683.6, filed Mar. 30, 2009 and U.S. Provisional Application No. 61/212,108 filed Apr. 6, 2009.

The present invention relates to a process for producing nano-fibrillar cellulose suspensions and the nano-fibrillar cellulose obtained by this process.

Cellulose is the structural component of the primary cell wall of green plants and is the most common organic compound on Earth. It is of high interest in many applications and industries.

Cellulose is the major constituent of paper and cardboard and of textiles made from cotton, linen, and other plant fibres. Cellulose can be converted into cellophane, a thin transparent film, and into rayon, an important fibre that has been used for textiles since the beginning of the 20th century. Both cellophane and rayon are known as "regenerated cellulose fibres".

Cellulose fibres are also used in liquid filtration, to create a filter bed of inert material. Cellulose is further used to make hydrophilic and highly absorbent sponges.

For industrial use, cellulose is mainly obtained from wood pulp and cotton. It is mainly used to produce cardboard and paper; and to a smaller extent it is converted into a wide variety of derivative products.

Cellulose pulp as a raw material is processed out of wood or stems of plants such as hemp, linen and manila. Pulp fibres are built up mainly from cellulose and other organic components (hemicellulose and lignin). The cellulose macromolecules (composed of 1-4 glycosidic linked β-D-Glucose molecules) are linked together by hydrogen bonds to form a so called primary fibril (micelle) which has crystalline and amorphous domains. Several primary fibrils (around 55) form a so called microfibril. Around 250 of these microfibrils form a fibril.

The fibrils are arranged in different layers (which can contain lignin and/or hemicellulose) to form a fibre. The individual fibres are bound together by lignin as well.

The pulps used in papermaking are often obtained by grinding the wood and an optional processing by heat and chemistry to remove undesired compounds from the cellulosic fibres.

The fibres are ground and cut to a certain fineness (depending on the desired properties). The grinding of the fibres is achieved with a refiner (such as a conic rotor-stator mill or disc- or double-disc refiners). The refiner also fibrillates the fibres on the surface which means that some fibrils are partially pulled out of the surface of the fibre. This leads to a better retention of, and, frequently, a better adhesion to, pigments which may be added in paper production, and also to an enhanced potential of hydrogen bonding between the fibres of the paper. This results in improved mechanical properties. A side-effect is also that the paper becomes denser and more transparent because of a loss of light scattering as the size of the scattering centres moves away from the accepted optimum of half the wave length of light (glassine and greaseproof papers).

When fibres become refined under applied energy they become fibrillated as the cell walls are broken and torn into attached strips, i.e. into fibrils. If this breakage is continued to separate the fibrils from the body of the fibre, it releases the fibrils. The breakdown of fibres into microfibrils is referred to as "micro fibrillation". This process may be continued until there are no fibres left and only fibrils of nano size (thickness) remain.

If the process goes further and breaks these fibrils down into smaller and smaller fibrils, they eventually become cellulose fragments. The breakdown to primary fibrils may be referred to as "nano-fibrillation", where there may be a smooth transition between the two regimes.

The achievable fineness with conventional refiners however is limited. Also, a number of other apparati for breaking down particles are not capable of breaking down cellulose fibres to nano-fibrils, such as fluffers mentioned in US 2001/0045264, which are only capable of separating given size fractions of fibres from each other.

Similarly, in WO 02/090651 a method for recycling pulp rejects generated during manufacturing of paper, paperboard or cardboard is described, wherein cleaner rejects containing among other things fibres, pigments and/or fibres are milled to a certain grain size by ball mills. However, no mention is made of the fibrillation of the fibres present, let alone the fibrillation into nano-fibrils.

If a further breakdown of the fibres into nano-fibrils is desired other methods are needed.

For example, in U.S. Pat. No. 4,374,702 a process for preparing microfibrillated cellulose is described comprising passing a liquid suspension of fibrous cellulose through a high pressure homogenizer having a small diameter orifice in which the suspension is subjected to a pressure drop of at least 3000 psi and a high velocity shearing action followed by a high velocity decelerating impact against a solid surface, repeating the passage of said suspension through the orifice until said cellulose suspension becomes a substantially stable suspension, said process converting said cellulose into microfibrillated cellulose without substantial chemical change of the cellulose starting material.

U.S. Pat. No. 6,183,596 B1 discloses a process for producing super microfibrillated cellulose by passing a slurry of a previously beaten pulp through a rubbing apparatus having two or more grinders which are arranged so that they can be rubbed together to microfibrillate the pulp to obtain microfibrillated cellulose and further super microfibrillate the obtained microfibrillated cellulose with a high-pressure homogenizer to obtain the super microfibrillated cellulose.

Furthermore, ultra-fine friction grinders can be used, wherein the grinder reduces the fibres into fines by mechanical shearing (cf. e.g. U.S. Pat. No. 6,214,163 B1).

There are a number of problems regarding the fibrillation of cellulose fibres, which have to be overcome.

For example, the mechanical production of nano-fibrillar cellulose often has the problem of an increasing viscosity during the fibrillation process. This can stop the process completely or increase the needed specific energy.

The efficiency of the breakdown processes often is rather low, and there is a considerable amount of fibres just cut, but not fibrillated into fibrils.

Therefore, there is a continuous need for providing more efficient processes for producing nano-fibrillar cellulose suspensions, and it is one objective of the present invention to provide a new and efficient process for the production of nano-fibrillar cellulose suspensions.

It has been found that the addition and co-processing of certain fillers and/or pigments with cellulose fibre containing pulp may have a positive influence on the fibrillating process in many respects, as described in more detail below.

Thus, the process of the present invention is characterized by the following steps:
(a) providing cellulose fibres;
(b) providing at least one filler and/or pigment;
(c) combining the cellulose fibres and the at least one filler and/or pigment;
(d) fibrillating the cellulose fibres in the presence of the at least one filler and/or pigment.

Nano-fibrillar cellulose in the context of the present invention means fibres, which are at least partially broken down to primary fibrils.

In this respect, fibrillating in the context of the present invention means any process which predominantly breaks down the fibres and fibrils along their long axis resulting in the decrease of the diameter of the fibres and fibrils, respectively.

Cellulose fibres, which can be used in the process of the present invention may be such contained in pulps selected from the group comprising eucalyptus pulp, spruce pulp, pine pulp, beech pulp, hemp pulp, cotton pulp, and mixtures thereof. In this respect, the use of kraft pulp, especially bleached long fibre kraft pulp may be especially preferred. In one embodiment, all or part of this cellulose fibre may be issued from a step of recycling a material comprising cellulose fibres. Thus, the pulp may also be recycled pulp.

The size of the cellulose fibres in principle is not critical. Useful in the present invention generally are any fibres commercially available and processable in the device used for their fibrillation. Depending on their origin, cellulose fibres may have a length of from 50 mm to 0.1 µm. Such fibres, as well as such having a length of preferably 20 mm to 0.5 µm, more preferably from 10 mm to 1 mm, and typically from 2 to 5 mm, can be advantageously used in the present invention, wherein also longer and shorter fibres may be useful.

It is advantageous for the use in the present invention that the cellulose fibres are provided in the form of a suspension, especially an aqueous suspension. Preferably such suspensions have a solids content of from 0.2 to 35 wt-%, more preferably 0.25 to 10 wt-%, especially 1 to 5 wt-%, and most preferably 2 to 4.5 wt-%, e.g. 1.3 wt-% or 3.5 wt-%.

The at least one filler and/or pigment is selected from the group comprising precipitated calcium carbonate (PCC); natural ground calcium carbonate (GCC); dolomite; talc; bentonite; clay; magnesite; satin white; sepiolite, huntite, diatomite; silicates; and mixtures thereof. Precipitated calcium carbonate, which may have vateritic, calcitic or aragonitic crystal structure, and/or natural ground calcium carbonate, which may be selected from marble, limestone and/or chalk, are especially preferred.

In a special embodiment, the use of ultrafine discrete prismatic, scalenohedral or rhombohedral precipitated calcium carbonate may be advantageous.

The fillers and/or pigments can be provided in the form of a powder, although they are preferably added in the form of a suspension, such as an aqueous suspension. In this case, the solids content of the suspension is not critical as long as it is a pumpable liquid.

In a preferred embodiment, the filler and/or pigment particles have a median particle size of from 0.5 to 15 µm, preferably 0.7 to 10 µm, more preferably 1 to 5 µm and most preferably 1.1 to 2 µm.

Especially preferably, the filler and/or pigment particles have a median particle size of from 0.03 to 15 µm, preferably 0.1 to 10 µm, more preferably 0.2 to 5 µm and most preferably 0.2 to 4 µm, e.g. 1.5 µm or 3.2 µm.

For the determination of the weight median particle size, $d_{50}$, for particles having a $d_{50}$ greater than 0.5 µm, a Sedigraph 5100 device from the company Micromeritics, USA was used. The measurement was performed in an aqueous solution of 0.1 wt-% $Na_4P_2O_7$. The samples were dispersed using a high-speed stirrer and ultrasound. For the determination of the volume median particle size for particles having a $d_{50} \leq 500$, a Malvern Zetasizer Nano ZS from the company Malvern, UK was used. The measurement was performed in an aqueous solution of 0.1 wt % $Na_4P_2O_7$. The samples were dispersed using a high-speed stirrer and ultrasound.

The fillers and/or pigments may be associated with dispersing agents such as those selected from the group comprising homopolymers or copolymers of polycarboxylic acids and/or their salts or derivatives such as esters based on, e.g. acrylic acid, methacrylic acid, maleic acid, fumaric acid, itaconic acid, e.g. acryl amide or acrylic esters such as methylmethacrylate, or mixtures thereof; alkali polyphosphates, phosphonic-, citric- and tartaric acids and the salts or esters thereof; or mixtures thereof.

The combination of fibres and at least one filler and/or pigment can be carried out by adding the filler and/or pigment to the fibres in one or several steps. As well, the fibres can be added to the filler and/or pigment in one or several steps. The filler and/or pigment as well as the fibres can be added entirely or in portions before or during the fibrillating step. However, the addition before fibrillating is preferred.

During the fibrillation process, the size of the fillers and/or pigments as well as the size of the fibres can change.

In one embodiment before fibrillating the pH of the combination of cellulose fibres and at least one filler and/or pigment is adjusted to a pH of 10 to 12, e.g. 11.

This adjustment to alkaline pH can be done via addition of preferably milk of lime ($Ca(OH)_2$) or any other base. After co-processing, the pH in the suspension might then have to be adjusted again to about 7.5 to 9.5, e.g. 8.5.

Generally, the pH of the suspension comprising the combination of fibres and pigment and/or filler should not be less than 6.

It might also be necessary to stabilize the pH, e.g. upon addition of PCC to a fibre suspension, which might lead to an increase of the pH, and a drop of the °SR. In this case the pH may be re-adjusted by commonly used acids or buffers in order to avoid the drop of the Schopper Riegler degree due to the influence of a pH increase.

Furthermore, in one embodiment, the combination is stored for 2 to 12 hours, preferably 3 to 10 hours, more preferably 4 to 8 hours, e.g. 6 hours, prior to fibrillating it, as this ideally results in swelling of the fibres facilitating the fibrillation and thus leads to a faster increase of freeness (°SR) and lower specific refining energy consumption for the same °SR freeness.

Fibre swelling may be facilitated by storage at increased pH, as well as by addition of cellulose solvents like, e.g. copper(II)ethylenediamine, iron-sodium-tartrate or lithium-chlotine/dimethylacetamine, or by any other method known in the art.

Preferably, the weight ratio of fibres to fillers and/or pigments on a dry weight basis is from 1:10 to 10:1, more preferably 1:6 to 6:1, typically 1:4 to 4:1, especially 1:3 to 3:1, and most preferably 1:2 to 2:1, e.g. 1:1.

For example, in one especially preferred embodiment 70 wt-% of bleached longfibre kraft pulp is fibrillated in the presence 30 wt-% ultrafine discrete prismatic (or rhombohedral) PCC, relating to the total dry weight of pulp and PCC, respectively.

One indication of cellulose fibrillation according to the present invention is the increase of the Schopper Riegler degree (°SR).

The Schopper-Riegler degree (°SR) is a measure of the rate at which a diluted pulp suspension may be de-watered and is specified according to the Zellcheming Merkblatt V 17/61 and standardized in ISO 5267/1.

The value is determined by smoothly dispersing the pulp in water and putting it into a drainage chamber where a sealing cone is closed. The sealing cone is lifted pneumatically from the drainage chamber, and, depending on the condition of the fibre suspension, the water flows more or less quickly from the drainage chamber through a side outlet into a measuring cylinder. The water is measured in the cylinder, wherein 10 ml water correspond to 1°SR, and the higher the Schopper-Riegler value, the finer the fibres.

For measuring the Schopper Riegler degree any devices suitable therefore can be used, such as the "Automatic Freeness Tester" supplied by Rycobel, Belgium.

Preferably the combination is fibrillated until the Schopper Riegler degree is increased by ≥4°SR, particularly ≥6°SR, more preferably ≥8°SR, most preferably ≥10°SR, especially ≥15°SR.

In a preferred embodiment the combination of fibres and filler and/or pigment is fibrillated until a final Schopper-Riegler degree of the resulting suspension of ≥30°SR, preferably ≥45°SR, more preferably ≥50 °SR, particularly ≥60°SR, e.g. ≥70°SR, especially ≥80°SR is reached.

In a special embodiment, it is however preferred that the final Schopper Riegler degree is ≤95 °SR.

The starting Schopper-Riegler degree may be from about 5 to about 90°SR, preferably it is ≤10°SR, preferably ≤25°SR, more preferably ≤40°SR, e.g. ≤60 or ≤75°SR. It may also be greater than 80°SR, if the Δ°SR resulting by the fibrillating step is ≤4°SR.

Looking at the Schopper Riegler degree, it has also been found that the process according to the present invention is much more efficient than fibrillating fibre suspensions in the absence of pigments and/or fillers.

This can be seen by an increased °SR per passage. In order to optimize the fibrillation, the fibre suspension is usually processed by subjecting it to several passages through the fibrillation device.

In this respect, it can be observed that according to the process of the present invention, the °SR per passage is markedly higher than with fibre suspensions only.

This effect can be immediately observed and occurs until a certain number of passages, when no further increase of the °SR is achieved any more.

Thus, in a special embodiment, the change in Schopper Riegler degree per passage is higher for the process of the present invention than for fibre suspensions fibrillated in the absence of pigment and/or filler, until no further essential increase can be observed in both cases.

Also, it can be observed that the simple addition of pigment and/or filler to an already fibrillated system does not in itself lead to as great an increase in the Schopper Riegler degrees as observed when fibrillating in the presence of pigment and/or filler.

Fibrillating is carried out by means of any device useful therefore, as mentioned above. Preferably the device is selected from the group comprising ultra-fine friction grinders such as a Super Mass Colloider, refiners, and homogenizers. In the case of fibrillating in a homogenizer and also in an ultra fine friction grinder, the temperature of the suspension in the homogenizer is preferably above 60° C., more preferably above 80° C. and even more preferably above 90° C.

Another aspect of the present invention is the suspension of nano-fibrillar cellulose obtained by the processes according to the invention.

Furthermore, an aspect of the invention is the advantageous use of the suspension of nano-fibrillar cellulose obtained by the processes according to the invention in paper manufacturing and/or paper finishing.

The nano-fibrillar cellulose suspensions according to the present invention can improve paper strength and may allow for an increase in filler load in uncoated freesheet papers.

Due to their mechanical strength properties the nano-fibrillar cellulose however is also advantageously used in applications such as in material composites, plastics, paints, rubber, concrete, ceramics, adhesives, food, or in wound-healing applications. The figures described below and the examples and experiments serve to illustrate the present invention and should not restrict it in any way.

EXAMPLES

1. Increase of °SR/Passage Using GCC

For examining the development of the °SR/passage, eucalyptus pulp with a °SR of 25 was treated first in an ultra-fine friction grinder at 4 wt-% solids content with and without the addition of GCC. A similar experiment was run on an homogenizer with eucalyptus pulp at 1.5 wt-% solids content with and without GCC.

Material
GCC: Omyacarb 1-AV (solids content 100 wt % based on weight of fibres present) available from Omya AG. The weight median particle size $d_{50}$=1.7 μm measured by Sedigraph 5100.

Omyacarb 10-AV (solids content 100 wt-% based on weight of fibres present) available from Omya AG. The weight median particle size $d_{50}$ is 10.0 μm measured by Sedigraph 5100.

Pulp: Eucalyptus pulp with 25°SR and an equivalent aqueous suspension pH of 7.6.

Example 1

Ultrafine Friction Grinder

For the comparative example eucalyptus pulp in the form of dry mats of 500 g per mat (700×1 000×1.5 mm) was used. 170 g pulp thereof was torn into pieces of 40×40 mm. 3 830 g tap water was added. The suspension was stirred in a 10 dm³ bucket at 2000 rpm using a dissolver disk with a diameter of 70 mm. The suspension was stirred for at least 15 minutes at 2000 rpm.

The suspension was then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 μm). The gap between the grinding stones was chosen to be the dynamic 0-point as described in the manual delivered by the supplier. The speed of the rotating grinder was adjusted to be 1200 rpm. The suspension was recirculated several times and samples were taken. The Schopper-Riegler degree (°SR) was measured according to the Zellcheming Merkblatt V/7/61 and standardized in ISO 5267/1.

For the inventive example eucalyptus pulp in the form of dry mats of 500 g per mat (700×1 000×1.5 mm) was used. 170 g pulp thereof was torn into pieces of 40×40 mm. 160 g Omyacarb 1-AV was added. 3 830 g tap water was added. The suspension was stirred in a 10 dm$^3$ bucket at 2000 rpm using a dissolver disk with a diameter of 70 mm. The suspension was stirred for at least 15 minutes at 2000 rpm. The suspension had a pH of about 7.5.

The suspension was then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 μm). The gap between the grinding stones was chosen to be the dynamic 0-point as described in the manual delivered by the supplier. The speed of the rotating grinder was adjusted to be 1200 rpm. The suspension was recirculated several times and samples were taken. The Schopper-Riegler degree (°SR) was measured according to the Zellcheming Merkblatt V/7/61 and standardized in ISO 5267/1. The additional filler was not considered for the requested 2 g/l pulp consistency for the measurement.

For the inventive example eucalyptus pulp in the form of dry mats of 500 g per mat (700×1 000×1.5 mm) was used. 170 g pulp thereof was torn into pieces of 40×40 mm. 160 g Omyacarb 10-AV was added. 3 830 g tap water was added. The suspension was stirred in a 10 dm$^3$ bucket at 2 000 rpm using a dissolver disk with a diameter of 70 mm. The suspension was stirred for at least 15 minutes at 2 000 rpm. The suspension had a pH of about 7.2.

The suspension was then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 μm). The gap between the grinding stones was chosen to be the dynamic 0-point as described in the manual delivered by the supplier. The speed of the rotating grinder was adjusted to be 1200 rpm. The suspension was recirculated several times and samples were taken. The Schopper-Riegler degree (°SR) was measured according to the Zellcheming Merkblatt V/7/61 and standardized in ISO 5267/1. The additional filler was not considered for the requested 2 g/l pulp consistency for the measurement.

Results

Figure 1:
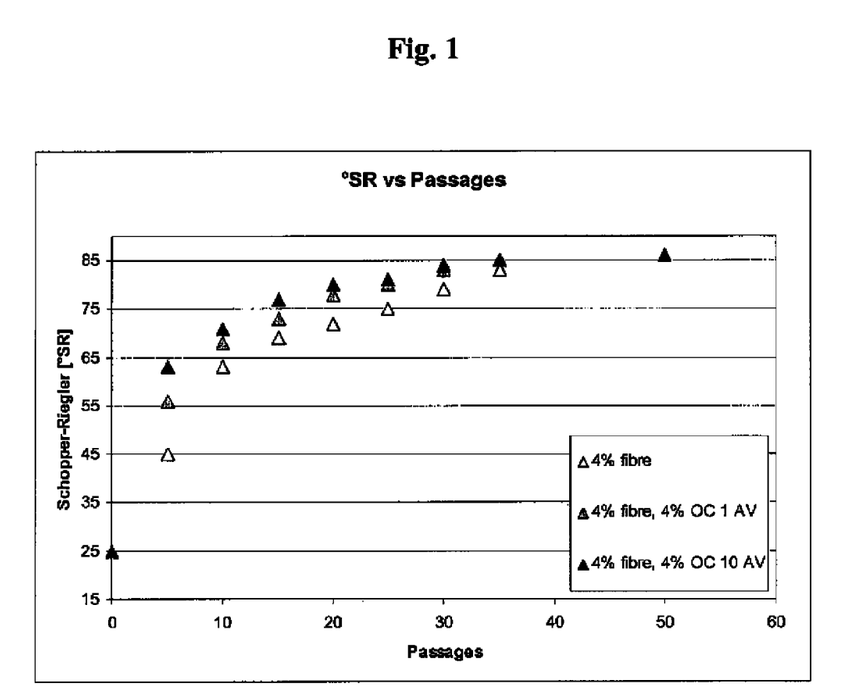
FIG. 1 shows the °SR/passage for pulp suspensions fibrillated with and without different natural ground calcium carbonates.

FIG. 1 shows the development of the °SR as a function of passages through the Sup ermasscolloider. It becomes apparent that the addition of GCC increases the efficiency of the device per passage.

Example 2

Homogenizer

For the comparative example eucalyptus pulp in the form of dry mats of 500 g per mat (700×1 000×1.5 mm) was used. 47 g pulp thereof was torn into pieces of 40×40 mm. 2953 g tap water was added. The suspension was stirred in a 5 dm$^3$ bucket at 2000 rpm using a dissolver disk with a diameter of 70 mm. The suspension was stirred for at least 15 minutes at 2000 rpm.

This suspension was fed into the Homogenizer (GEA Niro Soavi NS2006L) but did not run through the machine.

For the inventive example eucalyptus pulp in the form of dry mats of 500 g per mat (700×1000×1.5 mm) was used. 47 g pulp thereof was torn into pieces of 40×40 mm. 45 g Omyacarb 1-AV was added. 2953 g tap water was added. The suspension was stirred in a 5 dm$^3$ bucket at 2000 rpm using a dissolver disk with a diameter of 70 mm. The suspension was stirred for at least 15 minutes at 2000 rpm.

This suspension was fed into the Homogenizer (GEA Niro Soavi NS2006L). The flow through the homogenizer was between 100 and 200 g min$^{-1}$ and the pressure was adjusted to be between 200 and 400 bar. The suspension was recirculated several times and samples were taken. The Schopper-Riegler degree (°SR) was measured according to the Zellcheming Merkblatt V/7/61 and standardized in ISO 5267/1. The additional filler was not considered for the requested 2 g/l pulp consistency for the measurement.

Results

The comparative sample that contained no GCC could not be fed through the homogenizer. Only the GCC containing sample showed a good runnability. Schopper-Riegler values are reported in Table 1 after 5 and 10 passages through the homogenizer.

TABLE 1

| Passages | ° SR |
| --- | --- |
| 0 | 25 |
| 5 | 74 |
| 10 | 91 |

2. Increase of °SR Using PCC in a Refiner

Example 3

Ultrafine PCC

Material
PCC: Ultrafine prismatic PCC. The weight median particle size $d_{50}$=1.14 μm measured by Sedigraph 5100 (100 wt-% of particles have a diameter <2 μm; 27 wt-% of particles have a diameter <1 um).
This PCC was provided in the form of an aqueous suspension having a solids content of 7.9 wt-%.
Pulp: Longfibre bleached kraft pulp with 16°SR and an equivalent aqueous suspension pH of between 6 and 8.

An aqueous suspension was formed of the above carbonate and pulp such that this suspension had a solids content of approximately 4 wt-% and a carbonate:pulp weight ratio of 29:71.

Approximately 12.5 dm$^3$ of this suspension were circulated during a period of 9 minutes through an Esther Wyss R 1 L Labor-Refiner under 5.4 kW.

A Schopper-Riegler (°SR) of the obtained suspension of 92°SR was measured according to the Zellcheming Merkblatt V/7/61 and standardized in ISO 5267/1.

Example 4

Coarse PCC a) Suspension According to the Invention
Material
PCC: Scalenohedral PCC. The weight median particle size $d_{50}$=3.27 μm measured by Sedigraph 5100 (11 wt-% of particles have a diameter<2 μm; 4 wt-% of particles have a diameter<1 um). This PCC was provided in the form of an aqueous suspension having a solids content of 15.8%.

Pulp: Eucalyptus with 38°SR and an equivalent aqueous suspension pH of between 6 and 8.

An aqueous suspension was formed of the above carbonate and pulp such that this suspension had a solids content of approximately 9.8 wt-% and a carbonate:pulp weight ratio of 75:25. This suspension presented an 18°SR.

Approximately 38 m³ of this suspension was circulated during a period of 17.5 hours through a Metso Refiner RF-0 under 92 kW at a flow rate of 63 m³/hour.

A Schopper-Riegler (°SR) of the obtained suspension of 73°SR was measured according to the Zellcheming Merkblatt V/7/61 and standardized in ISO 5267/1.

b) Comparative Suspension
Material

PCC: Scalenohedral PCC. The weight median particle size $d_{50}$=3.27 μm measured by Sedigraph 5100 (11 wt-% of particles have a diameter<2 μm; 4 wt-% of particles have a diameter<1 μm). This PCC was provided in the form of an aqueous suspension having a solids content of 15.8%.

Pulp: Eucalyptus with 38°SR and an equivalent aqueous suspension pH of between 6 and 8.

An aqueous suspension was formed of the above pulp such that this suspension had a solids content of approximately 4.5 wt-%.

Approximately 20 m³ of this suspension was circulated during a period of 17.5 hours through a Metso Refiner RF-0 under 92 kW at a flow rate of 63 m³/hour.

A Schopper-Riegler (°SR) of the obtained suspension of 65°SR was measured according to the Zellcheming Merkblatt V/7/61 and standardized in ISO 5267/1.

To this suspension, the above scalenohedral PCC was added in an amount so as to obtain a carbonate : pulp weight ratio of 75:25. A Schopper-Riegler (°SR) of the obtained suspension of 25°SR was measured according to the Zellcheming Merkblatt V/7/61 and standardized in ISO 5267/1.

This clearly shows that the presence of calcium carbonate during the fibrillation step is essential for obtaining a high Schopper Riegler degree, i.e. an efficient fibrillation of the cellulose fibres.

3. Increase of °SR/Passage Using Different Fillers or Pigments and/or Different Pulps For examining the development of the °SR/passage, eucalyptus or pine pulp was treated in an ultra-fine friction grinder with the addition of the filler or pigment as indicated here below.

Material

GCC: Aqueous suspension of natural ground calcium carbonate dispersed with polymeric acrylic acid-based dispersant, solids content 50 wt-%). The volume median particle size $d_{50}$ is 246 nm measured by Malvern Zetasizer Nano ZS.

Talc: Finntalc F40 available from Mondo Minerals.

Pulp: Eucalyptus pulp in the form of dry mats, with 17 to 20°SR, a brightness of 88.77% (ISO 2470-2) and an equivalent aqueous suspension pH of between 7 and 8.

Pine pulp in the form of dry mats, with 17 to 20°SR, a brightness of 88.19% (ISO 2470-2) and an equivalent aqueous suspension pH of between 7 and 8.

Example 5

Ultrafine Friction Grinder

In the following examples, the pulp indicated in the Table below, in the form of dry mats, was used. 90 g pulp thereof was torn into pieces of 40×40 mm. The filler indicated in the Table below was added in the indicated amount, along with 2 190 g of tap water. The suspensions were each stirred in a 10 dm³ bucket at 2000 rpm using a dissolver disk with a diameter of 70 mm. The suspensions were each stirred for at least 10 minutes at 2000 rpm.

The suspensions were then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 μm). Prior to commencing the following tests, the gap between the grinding stones was set to be the dynamic 0-point as described in the manual delivered by the supplier. For each the tests below, the gap between the grinding stones were further closed from this 0-point by 5 increments, corresponding to an adjustment of −50 μm, as soon as the first material passed between the stones. The speed of the rotating grinder was adjusted to be 2000 rpm for the first 5 passages, and decreased to 1500 rpm for passage 6 and to 1000 rpm for passage 7. Following each passage, the rpm of the friction grinder was increased to approximately 2600 rpm for a period of 5 seconds in order to ensure that a maximum of materials was extracted from the friction grinder before commencing the following passage directly thereafter. The Schopper-Riegler degree (°SR) was measured according to the Zellcheming Merkblatt V/7/61 and standardized in ISO 5267/1. The additional filler was not considered for the requested 2 g/l pulp consistency for the measurement. So the pulp consistency was constant for Tests a and b at 2 g/l.

| Test | a) | b) |
|---|---|---|
| Type pulp: | Eucalyptus | Pine |
| Type filler/pigment | GCC | Finntalc F40 |
| Amount filler/pigment (g dry, [g suspension]) | 90 g [180 g] | 90 g |
| Weight ratio filler/pigment:fibre | 1:1 | 1:1 |

Results

Figure 2:
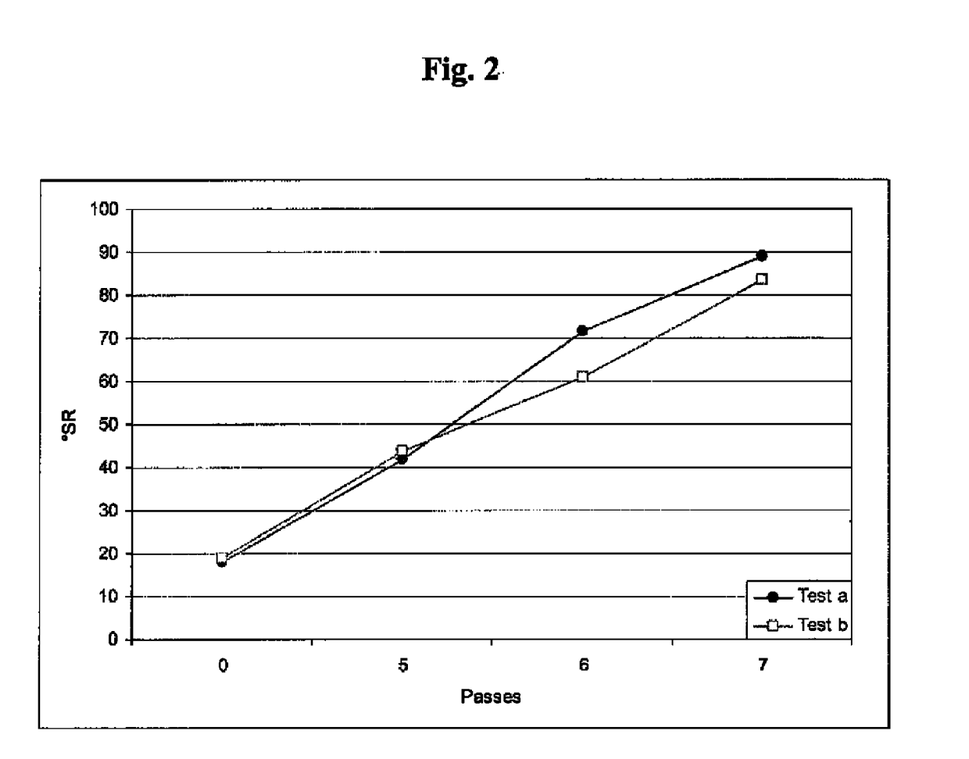
FIG. 2 shows the °SR/passage for pulp suspensions fibrillated with different fillers/pigments.

FIG. 2 shows the development of the °SR as a function of passages through the Supermasscolloider. It becomes apparent that the addition of filler results in an efficient °SR development in the device per passage (compared to tests g and f below), also for other pulp types than Eucalyptus and other filler types than GCC and PCC.

4. Increase of °SR/Passage of Comparative Example Treating Pulp in a Ball Mill with and Without GCC For examining the development of the °SR/passage, eucalyptus pulp was treated in a ball mill with and without the addition of the filler or pigment as indicated here below.

Material

GCC: Omyacarb 1-AV in the form of a powder, available from Omya AG. The weight median particle size $d_{50}$=1.7 μm measured by Sedigraph 5100.

Pulp: Eucalyptus pulp in the form of dry mats, with 17 to 20°SR, a brightness of 88.77% (ISO 2470-2) and an equivalent aqueous suspension pH of between 7 and 8.

Example 6

Ball Mill

In the following examples, the pulp indicated in the table below, in the form of dry mats, was used. 88 g pulp thereof was torn into pieces of 40×40 mm. Omyacarb 1-AV was added in the amount indicated in the Table below, along with 5000 g of tap water. The suspensions were each stirred in a 10 dm³ bucket at 2000 rpm using a dissolver disk with a diameter of 70 mm. The suspensions were each stirred for at least 10 minutes at 2000 rpm.

1600 g of each suspension was then introduced in a 3 dm³ porcelain vessel filled with 3500 g of Verac beads having a bead diameter of 2 cm. The vessel was closed and rotated 43 rpm for a period of 24 hours. The Schopper-Riegler degree (°SR) was measured according to the Zellcheming Merkblatt V/7/61 and standardized in ISO 5267/1. The additional filler was not considered for the requested 2 g/l pulp consistency for the measurement. So the pulp consistency was constant for Tests c and d at 2 g/l.

| Test | c) | d) |
|---|---|---|
| Type pulp | Eucalyptus | Eucalyptus |
| Type filler/pigment | None | Omyacarb 1-AV |
| Amount filler/pigment (g dry, [g suspension]) | 0 g | 28.2 g |
| Weight ratio filler/pigment:fibre | n/a | 1:1 |

Results

Figure 3:
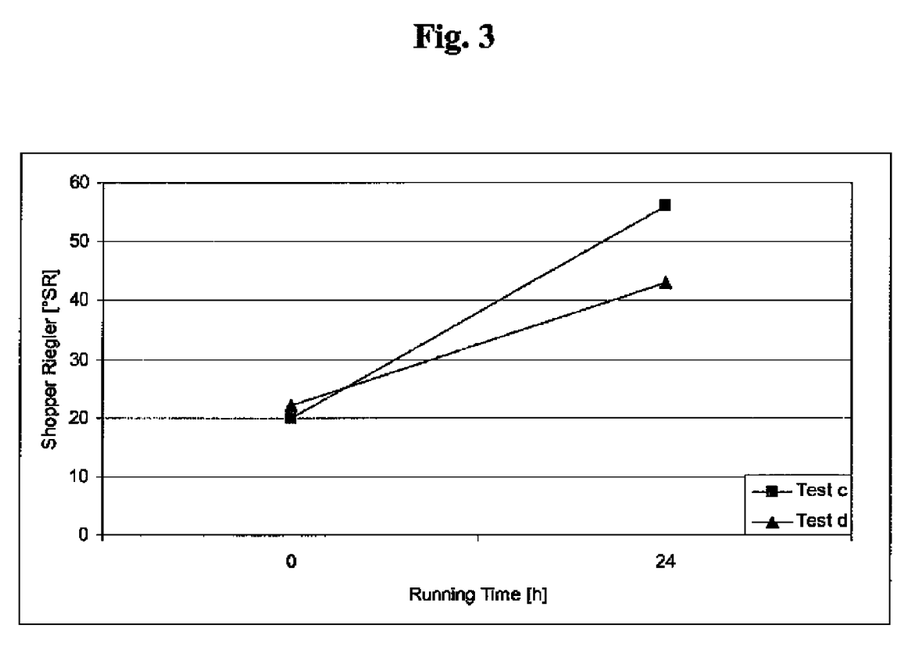
FIG. 3 shows the °SR/running time for pulp suspensions ground in a ball mill with and without natural ground calcium carbonate.

FIG. 3 shows the development of the °SR as a function of passages through the ball mill. It is apparent that the addition of filler does not positively influence the °SR development in the device over time.

5. Beneficial Effect of Filler

Example 7

Ultrafine Friction Grinder

Tests e to g were processed with an ultra-fine friction grinder (Supermasscolloider from Masuko Sangyo Co. Ltd, Japan (Model MKCA 6-2) with mounted silicon carbide stones having a grit class of 46 (grit size 297-420 µm). The gap between the stones was adjusted to "−50" µm (dynamic 0-point, as described in the manual delivered by the supplier). The speed of the rotating grinder was set to 2000 rpm for passes 1-5, to 1500 rpm for pass 6 and to 1000 rpm for pass 7. Samples for Shopper-Riegler degree measurements were taken before grinding, after passes 5, 6 and 7. The Shopper-Riegler degree (°SR) was measured according to the Zellcheming Merkblatt V/7/61 and standardized in ISO 5267/1. The additional filler was not considered for the requested 2 g/l pulp consistency for the measurement. So the pulp consistency was constant for all tests e to g at 2 g/l.

Material:

Omyacarb 1 AV Omyacarb 1-AV available from Omya AG; Fine calcium carbonate powder, manufactured from a high purity, white marble; The weight median particle size $d_{50}$ is 1.7 µm measured by Sedigraph 5100.

Eucalyptus pulp Dry mat, brightness: 88.77% (ISO 2470-2), equivalent pulp suspension pH between 7 and 8 and °SR between 17 and 20

Test e):

90 g dry Eucalyptus pulp, 2910 g tap water and 90 g Omyacarb 1 AV (1:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph. Samples were taken and measured as described above in the according paragraph.

Test f) (Comparative Test):

90 g dry Eucalyptus pulp and 2910 g tap water were mixed using a Pendraulik stirrer at 2000 rpm with a mounted dissolver disk (d=70 mm) for at least 10 minutes. This mixture was processed with the Supermasscolloider as described above in the according paragraph. Samples were taken and measured as described above in the according paragraph.

Test g) (Comparative Test):

Same as test f) but 90 g Omyacarb 1 AV added after fibrillation.

Results

Figure 4:
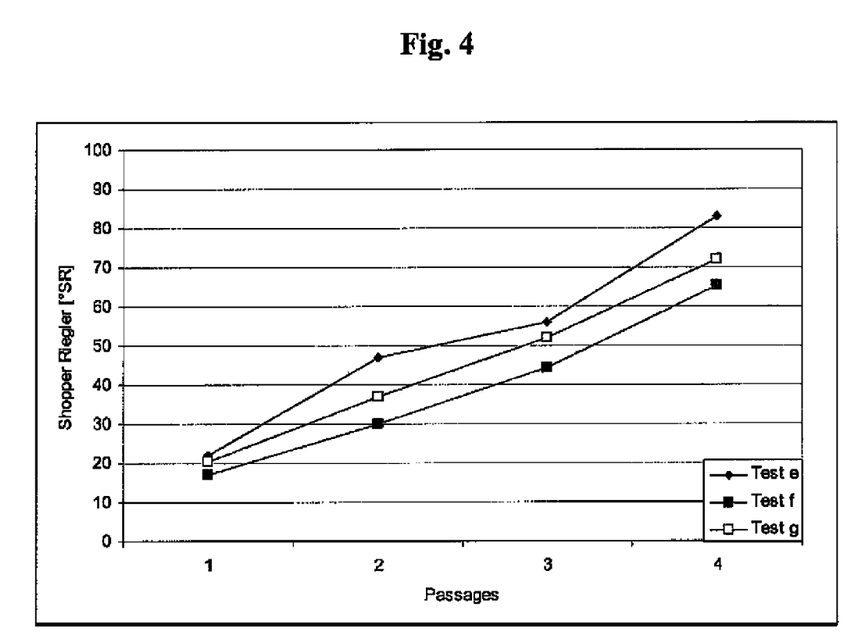
FIG. 4 shows the °SR/running time for pulp suspensions ground with and without natural ground calcium carbonate added before or after fibrillation.

FIG. 4 shows that the addition of filler (test g) to a nano-cellulosic suspension that was produced in the absence of filler (test f) leads to increased °SR values, but not to a change of steepness (that means no efficiency increase).

However a nanocellulosic suspension that was produced in the presence of filler (test e) shows a higher increase of °SR compared to the comparative tests (g and f).

6. Use of Nano-Fibrillar Cellulose Suspension in Paper Making 60 g dry of a sulphated paste of wood and fibres composed of 80% birch and 20% pine, with a freeness value of 23°SR, is diluted in 10 dm³ of water. To this dilution is added approximately 1.5 g dry of the nano-fibrillar cellulose suspension produced according to Example 1 using Omyacarb 1-AV, as well as a 62 wt-% suspension of a pre-dispersed natural ground calcium carbonate (marble) having a microcrystalline, rhombohedral particle shape and a weight median particle size $d_{50}$ of 0.8 µm (measured by Sedigraph 5100). The latter is added in an amount so as to obtain an overall filler content of 30+/−0.5% based on the final paper weight. After 15 minutes of agitation and following addition of 0.06% by dry weight, relative to the dry weight of the paper, of a polyacrylamide retention aid, a sheet with a grammage of 75 g/m² is formed using Rapid-Kothen type hand sheet former.

The invention claimed is:

1. A process for the production of a nano-fibrillar cellulose suspension comprising the steps of:
   (a) providing cellulose fibres;
   (b) providing a filler;
   (c) combining the cellulose fibres from step (a) and the filler from step (b); and
   (d) fibrillating the cellulose fibres and the filler from step (c) to obtain a nano-fibrillar cellulose suspension,
   wherein the filler is calcium carbonate, and wherein in step (d) the weight ratio of fibres to filler on a dry weight basis is from 1:10 to 10:1.

2. The process according to claim 1, wherein the cellulose fibres in step (a) are contained in pulps selected from eucalyptus pulp, spruce pulp, pine pulp, beech pulp, hemp pulp, cotton pulp, or any mixture thereof.

3. The process according to claim 1, wherein the cellulose fibres in step (a) are contained in kraft pulp.

4. The process according to claim 1, wherein the cellulose fibres in step (a) are contained in bleached longfibre kraft pulp.

5. The process according to claim 1, wherein the cellulose fibres in step (a) are provided in the form of a suspension.

6. The process according to claim 1, wherein the cellulose fibres in step (a) are provided in the form of a suspension at a solids content of from 0.2 to 35 wt-%.

7. The process according to claim 1, wherein the cellulose fibres in step (a) are provided in the form of a suspension at a solids content of from 0.25 to 10 wt-%.

8. The process according to claim 1, wherein the cellulose fibres in step (a) are provided in the form of a suspension at a solids content of from 1 to 5 wt-%.

9. The process according to claim 1, wherein the cellulose fibres in step (a) are provided in the form of a suspension at a solids content of from 2 to 4.5 wt-%.

10. The process according to claim 1, wherein the cellulose fibres in step (a) are provided in the form of a suspension at a solids content of about 1.3 or about 3.5 wt-%.

11. The process according to claim 1, wherein the filler in step (b) is precipitated calcium carbonate.

12. The process according to claim 1, wherein the filler in step (b) is precipitated calcium carbonate having a vateritic, a calcitic or an aragonitic crystal structure.

13. The process according to claim 1, wherein the filler in step (b) is natural ground calcium carbonate.

14. The process according to claim 1, wherein the filler in step (b) is natural ground calcium carbonate selected from marble, limestone and/or chalk.

15. The process according to claim 11, wherein the precipitated calcium carbonate in step (b) is ultrafine discrete prismatic, scalenohedral or rhombohedral precipitated calcium carbonate.

16. The process according to claim 1, wherein the filler in step (b) is in the form of particles having a median particle size of from 0.03 to 15 μm.

17. The process according to claim 1, wherein the filler in step (b) is in the form of particles having a median particle size of from 0.2 to 5 μm.

18. The process according to claim 1, wherein the filler in step (b) is in the form of particles having a median particle size of from 0.2 to 4 μm.

19. The process according to claim 1, wherein the filler particles in step (b) is in the form of particles having a median particle size of about 1.5 or about 3.2 μm.

20. The process according to claim 1, wherein the filler in step (b) comprises a dispersing agent.

21. The process according to claim 20, wherein the dispersing agent is selected from homopolymers or copolymers of polycarboxylic acids and/or their salts or esters, acrylic acid, methacrylic acid, maleic acid, fumaric acid, itaconic acid, acryl amide or acrylic esters, or mixtures thereof; alkali polyphosphates, phosphonic-, citric- or tartaric acids, salts or esters thereof; or mixtures thereof.

22. The process according to claim 1, wherein before fibrillating in step (d), the pH of the combination of the cellulose fibres and the filler is adjusted to a pH of 10 to 12.

23. The process according to claim 1, wherein after fibrillating in step (d), the pH of the suspension is re-adjusted to a pH of 7.5 to 9.5.

24. The process according to claim 1, wherein after fibrillating in step (d), the pH of the suspension is re-adjusted to a pH of about 8.5.

25. The process according to claim 1, wherein the combination resulting from step (c) is stored for 2 to 12 hours prior to fibrillating in step (d).

26. The process according to claim 1, wherein the combination resulting from step (c) is stored for 3 to 10 hours, prior to fibrillating in step (d).

27. The process according to claim 1, wherein the combination resulting from step (c) is stored for 4 to 8 hours, prior to fibrillating in step (d).

28. The process according to claim 1, wherein a cellulose solvent is added to the combination in step (c) prior to fibrillating in step (d).

29. The process according to claim 28, wherein the cellulose solvent is copper(II)ethylenediamine, iron-sodium-tartrate or lithium-chloride/ dimethylacetamine.

30. The process according to claim 1, wherein in step (d) the weight ratio of fibres to filler on a dry weight basis is from 1:6 to 6:1.

31. The process according to claim 1, wherein in step (d) the weight ratio of fibres to filler on a dry weight basis is from 1:4 to 4:1.

32. The process according to claim 1, wherein in step (d) the weight ratio of fibres to filler on a dry weight basis is from 1:3 to 3:1.

33. The process according to claim 1, wherein in step (d) the weight ratio of fibres to filler on a dry weight basis is from 1:2 to 2:1.

34. The process according to claim 1, wherein in step (d) 70 wt-% of bleached longfibre kraft pulp is fibrillated in the presence 30 wt-% ultrafine discrete prismatic or rhombohedral precipitated calcium carbonate (PCC), relative to the total dry weight of pulp and PCC, respectively.

35. The process according to claim 1, wherein the combination from step (c) is fibrillated in step (d) until a Schopper Riegler degree is increased by ≥4°SR.

36. The process according to claim 1, wherein the combination from step (c) is fibrillated in step (d) until a Schopper Riegler degree is increased by ≥6°SR.

37. The process according to claim 1, wherein the combination from step (c) is fibrillated in step (d) until a Schopper Riegler degree is increased by ≥8°SR.

38. The process according to claim 1, wherein the combination from step (c) is fibrillated in step (d) until a Schopper Riegler degree is increased by ≥10°SR.

39. The process according to claim 1, wherein the combination from step (c) is fibrillated in step (d) until a Schopper Riegler degree is increased by ≥15°SR.

40. The process according to claim 1, wherein the combination of fibres and filler from step (c) is fibrillated in step (d) until a final Schopper-Riegler degree of ≥30°SR is reached.

41. The process according to claim 1, wherein the combination of fibres and filler from step (c) is fibrillated in step (d) until a final Schopper-Riegler degree of ≥45°SR is reached.

42. The process according to claim 1, wherein the combination of fibres and filler from step (c) is fibrillated in step (d) until a final Schopper-Riegler degree of ≥50°SR is reached.

43. The process according to claim 1, wherein the combination of fibres and filler from step (c) is fibrillated in step (d) until a final Schopper-Riegler degree of ≥60°SR is reached.

44. The process according to claim 1, wherein the combination of fibres and filler from step (c) is fibrillated in step (d) until a final Schopper-Riegler degree of ≥70°SR is reached.

45. The process according to claim 1, wherein the combination of fibres and filler from step (c) is fibrillated in step (d) until a final Schopper-Riegler degree of ≥80°SR is reached.

46. The process according to claim 1, wherein the fibrillating in step (d) is carried out by a device selected from an ultra-fine friction grinder, a refiner, or a homogenizer.

47. The process according to claim 1, wherein the fibrillating in step (d) is carried out by an ultra-fine friction grinder or a homogenizer, and wherein the temperature of the suspension in the ultra-fine friction grinder or the homogenizer is above 60° C.

48. The process according to claim 1, wherein the fibrillating in step (d) is carried out by an ultra-fine friction grinder or a homogenizer, and wherein the temperature of the suspension in the ultra-fine friction grinder or the homogenizer is above 80° C.

49. The process according to claim 1, wherein the fibrillating in step (d) is carried out by an ultra-fine friction grinder or a homogenizer, and wherein the temperature of the suspension in the ultra-fine friction grinder or the homogenizer is above 90° C.

50. A process for the production of a nano-fibrillar cellulose suspension comprising the steps of:

(a) providing cellulose fibres;
(b) providing a filler;
(c) combining the cellulose fibres from step (a) and the filler from step (b); and
(d) fibrillating the cellulose fibres and the filler from step (c) to obtain a nano-fibrillar cellulose suspension,
wherein the filler comprises calcium carbonate and one or more of dolomite, talc, bentonite, clay, magnesite, satin white, sepiolite, huntite, diatomite, and a silicate, and wherein in step (d) the weight ratio of fibres to filler on a dry weight basis is from 1:10 to 10:1.

* * * * *